US00PP37478P2

(12) United States Plant Patent
Pinedo

(10) Patent No.: US PP37,478 P2
(45) Date of Patent: Jun. 23, 2026

(54) ***CARISSA* PLANT NAMED 'Lemon Twist'**

(50) Latin Name: *Carissa macrocarpa*
Varietal Denomination: Lemon Twist

(71) Applicant: Pinedo Nursery, Inc., Ontario, CA (US)

(72) Inventor: Oscar Pinedo, Ontario, CA (US)

(73) Assignee: Pinedo Nursery, Inc., Ontario, CA (US)

( * ) Notice: Subject to any disclaimer, the term of this patent is extended or adjusted under 35 U.S.C. 154(b) by 0 days.

(21) Appl. No.: 19/045,887

(22) Filed: Feb. 5, 2025

(51) Int. Cl.
*A01H 5/00* (2018.01)
*A01H 6/08* (2018.01)

(52) U.S. Cl.
USPC ..... Plt./226
CPC ..... *A01H 6/08* (2018.05)

(58) Field of Classification Search
USPC ..... Plt./226
See application file for complete search history.

(56) References Cited

PUBLICATIONS www.https://plants.usda.gov/basic-search-results- Retrieved from the Internet on Nov. 4, 2025.*

* cited by examiner

*Primary Examiner* — Susan Mccormick Ewoldt
(74) *Attorney, Agent, or Firm* — Weatherly IP Solutions, LLC; James M. Weatherly

(57) ABSTRACT

A new variety of *Carissa* named 'Lemon Twist' which exhibits striking green and lemon-yellow variegated foliage, becoming green and cream as the season progresses, is disclosed.

2 Drawing Sheets

Genus and species: *Carissa macrocarpa.*
Variety denomination: 'Lemon Twist'.

BACKGROUND

The present invention relates to a new and distinct cultivar of *Carissa* plant, sometimes known as Natal Plum in recognition of its native origin, Natal Province, South Africa and its production of showy plum-like fruit which are edible. *Carissa macrocarpa* is grown as a showy evergreen ornamental plant for planting in containers, as solitary landscape plants and for hedging. *Carissa* has become naturalized in Florida due to its invasive self-propagation by layering (node rooting) of ground covering stems. *Carissa* is not hardy but is tolerant of drought and salt-laden winds. When grown in containers, plants of *Carissa* require full sun or light shade and limited irrigation. Container plants of *Carissa* will require indoor or greenhouse protection during the winter months.

The new variety is known botanically as *Carissa macrocarpa* and will be referred to hereinafter by the cultivar name 'Lemon Twist'.

The inventor discovered 'Lemon Twist' as a naturally occurring variegated branch sport found growing on an evergreen plant of *Carissa macrocarpa* 'Green Carpet' (unpatented). The inventor discovered 'Lemon Twist' in 2000 amongst a commercial crop of *Carissa* 'Green Carpet' which the inventor had raised and grown at their Ontario, California plant nursery which specializes in plants suitable for Southern California gardens and landscapes. 'Lemon Twist' exhibits striking green and lemon-yellow variegated foliage, becoming green and cream as the season progresses. 'Lemon Twist' produces occasional solitary white, fragrant, star-shaped flowers in spring and summer.

'Lemon Twist' can be compared with its sport parent, *Carissa* 'Green Carpet' by foliage variegation. Whereas both surfaces of the leaves of *Carissa* 'Green Carpet' is entirely green in color, the upper surfaces of the foliage of 'Lemon Twist' are strikingly variegated consisting of mid-green to dark-green asymmetrical patches surrounded by white to light cream marginal bands. The under surfaces of 'Lemon Twist' are not variegated except for a pale cream margin around an entirely pale green blade.

'Lemon Twist' was first asexually propagated by the inventors at their nursery in Ontario, California using the method of stem cuttings which were directly inserted into 1-gallon containers. Rooting and plant establishment is rapid and vigorous at ambient temperatures in Southern California, around 20° C. to 24° C.

The inventors have carried out multiple asexual reproductions and have confirmed that the variegation of 'Lemon Twist' is uniform and stable and reproduces true to type from its cuttings.

SUMMARY

The following traits have been repeatedly observed and represent the distinguishing characteristics of the new *Carissa* variety known as 'Lemon Twist'. These traits in combination distinguish 'Lemon Twist' from all other existing varieties of *Carissa* known to the inventor. 'Lemon Twist' has not been tested under all possible conditions and phenotypic differences may be observed with variations in environmental, climatic, and cultural conditions, however, without any variance in genotype. Growing requirements are similar to the species.

1. 'Lemon Twist' exhibits an exceptionally low-growing and spreading plant habit.

2. 'Lemon Twist' exhibits striking green and cream to yellow variegated glossy foliage.
3. The branches of 'Lemon Twist' bear stiff and strong thorns or spines at their terminals, either singly or as forked pairs.
4. 'Lemon Twist' produces occasional pure white colored flowers borne at the base of the terminal spines or the base of a pair of spikes.
5. The petals of the flowers of 'Lemon Twist' are free, rotate and white in color, glabrous and sweetly fragrant.
6. Mature plants of 'Lemon Twist' are low maintenance and reach 30 cm-60 cm in height and spread to 1.2 m in width.
7. 'Lemon Twist' blooms rarely from late spring through summer.
8. 'Lemon Twist' is hardy to USDA Zone 9 and is tolerant of high heat and humidity.

BRIEF DESCRIPTION OF THE DRAWINGS

The accompanying color drawings illustrate the overall appearance of the new *Carissa* variety named 'Lemon Twist' showing colors as true as it is reasonably possible to obtain in colored reproductions of this type.

The drawing labeled

The drawing labeled

Figure 1:
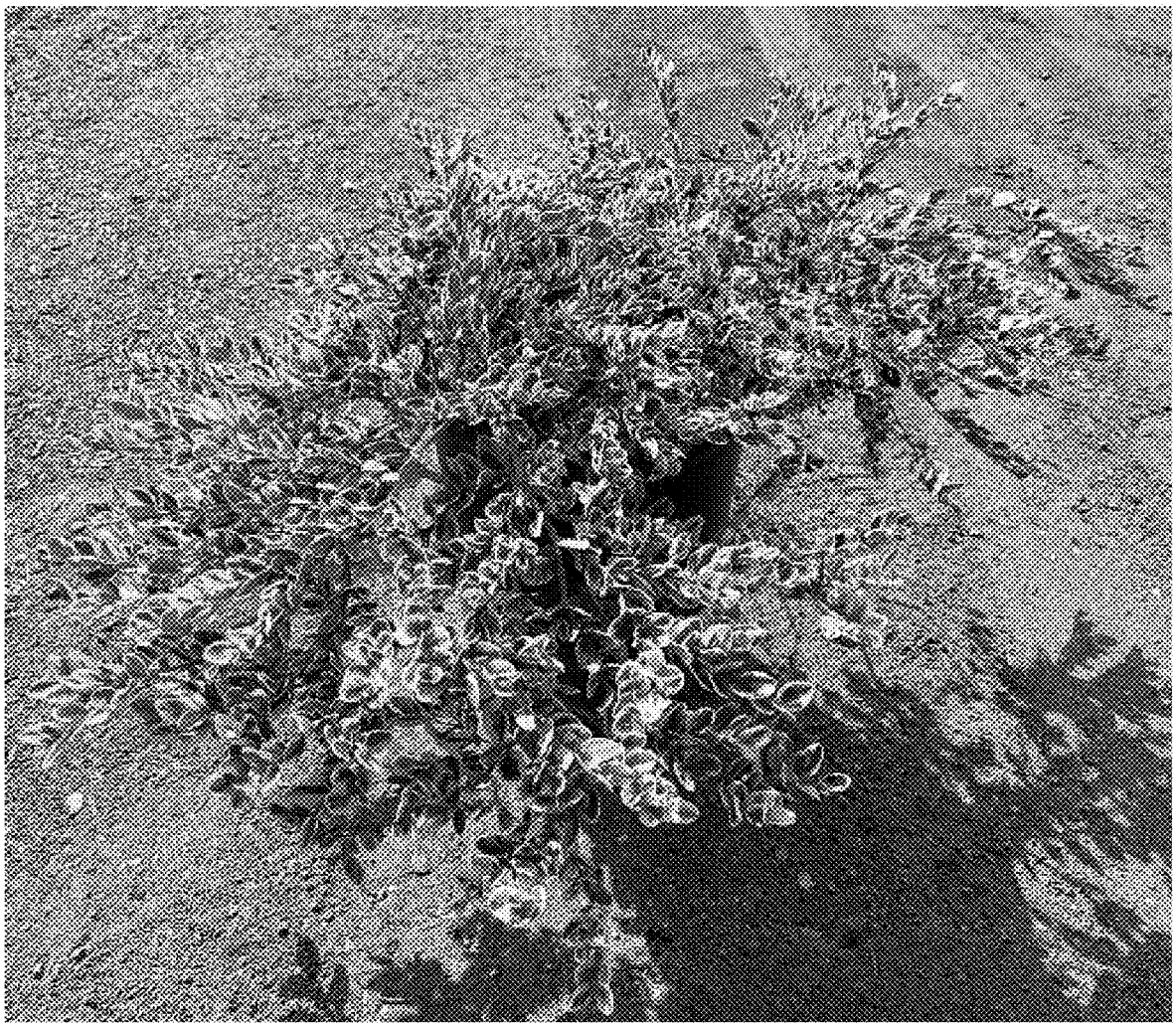
FIG. 1 depicts the variegated foliage of 'Lemon Twist' growing on a one year old plant which has been established in a 1-gallon container in Ontario, California. The illustrated plant has been grown in sun under very light shade.
Figure 2:
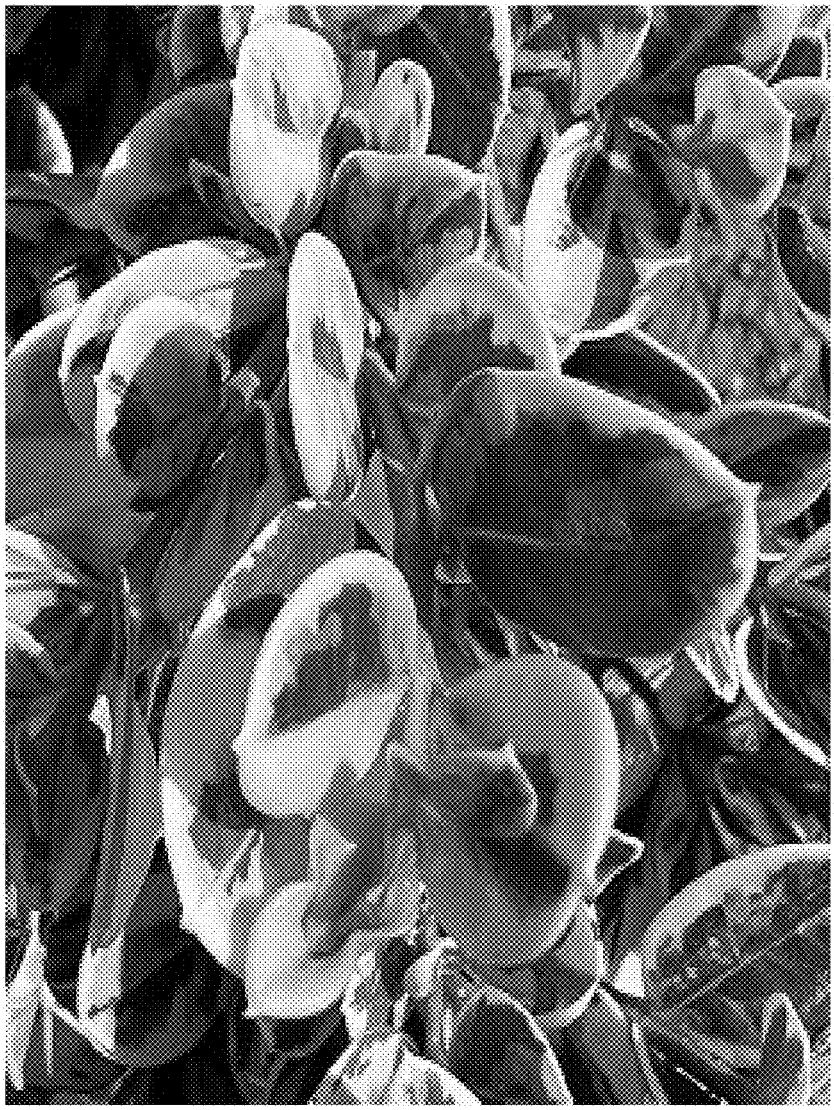
FIG. 2 depicts a close-up view of the range of variegation in the foliage of 'Lemon Twist'.

Colors in the drawing may differ from color values cited in the detailed botanical description, which accurately describe the actual color of the new *Carissa* variety named 'Lemon Twist'. All drawings were made using conventional techniques and although foliage colors may appear different from actual colors due to light reflectance, they are as accurate as possible by conventional photography.

BOTANICAL DESCRIPTION OF THE PLANT

The following is a detailed description of the new *Carissa* cultivar named 'Lemon Twist'. Data was collected in Santa Barbara, California in August 2024 from an established 15-month-old plant which was growing out of doors in very light shade in a 2-gallon container. Phenotypic differences may be observed with variations in environmental, climatic, and cultural conditions, without however, any difference in genotype. Color determinations are in accordance with the fifth edition (2007) of The Royal Horticultural Society Colour Chart except where general color terms of ordinary dictionary significance are used. The growing requirements are similar to the species.

Classification:

*Family*.—Apocynaceae.

*Genus and species*.—*Carissa macrocarpa*.

*Denomination*.—'Lemon Twist'.

*Common name*.—Natal Plum.

Plant parentage: 'Lemon Twist' is a naturally occurring branch sport of a plant of *Carissa macrocarpa* 'Green Carpet' (unpatented).

Plant description:

*Plant type*.—Evergreen non-hardy landscape or container plant.

*Plant use*.—Solitary container or landscape planting, barrier plant when planted as a hedge.

*Plant vigor*.—Slow spreading growth and very slow upright growth.

*Branching habit*.—Profuse basal and nodal branching.

*Dimensions at maturity*.—30 cm to 60 cm in height and spread to 1.2 m in width.

*Plant hardiness*.—USDA Zone 9.

*Asexual propagation method*.—Softwood cuttings bearing multiple leaves with lower leaves removed. No rooting hormone is required.

*Growth habit*.—Low mounding and spreading. Stems may root where a node is in contact with soil surface. Variety makes a good ground cover.

*Root system*.—Fine and fibrous. Root color 163D.

*Cultural requirements*.—Plant in well-draining soil, in good light but avoiding direct unfiltered sun. Ensure that rooting zone remains moist but not excessively wet. The incorporation of sharp grit in the planting mix will encourage root growth and minimize waterlogging.

*Planting conditions*.—'Lemon Twist' is both drought-tolerant and humidity tolerant.

*Time to initiate roots*.—2 weeks to develop roots on an initial cutting at soil and air temperatures around 20° C. to 24° C.

*Crop time*.—8 to 10 weeks from a rooted cutting to a finished commercial 1-litre container. Seasonal interest: Flowers from late spring and early summer.

*Disease and pest resistance*.—No disease or pest resistance has been identified.

Stems:

*Stem shape*.—Cylindrical, stem terminates with stout spines borne singly or bifurcated in pairs.

*Stem surface*.—Glabrous.

*Stem length*.—Unpinched primary stems: 30 cm to 45 cm in length, 2 mm to 4 mm in diameter.

*Stem length* (*lateral stems*).—10 cm to 15 cm in length, 2 mm to 3 mm in diameter.

*Stem color*.—Juvenile (new) stem growth pale yellow-green 1A to 11B with light coloration 39B in full sun exposure. Established stems 137D.

*Internodal distance*.—Very short, 2 mm to 3 mm.

Foliage:

*Leaf length*.—55 mm.

*Leaf width*.—35 mm.

*Leaf arrangement*.—Opposite.

*Leaf division*.—Simple.

*Leaf shape*.—Broadly ovate.

*Leaf apex*.—Acute.

*Leaf base*.—Cuneate.

*Leaf texture* (*both surfaces*).—Smooth, leathery and waxy.

*Leaf attachment*.—Sessile.

Variegation:

*Adaxial surfaces*.—Patches of mid-green to dark grey-green patches occupy between 40% and 80% of surface. All leaves bear at least a narrow cream margin (minimum of 3 mm in width) which may extend inwards to occupy up to 80% of the leaf surface.

*Abaxial surfaces*.—Leaves are uniformly 139A (mid grey-green) with very narrow 1D (cream) margin (1 mm to 2 mm in width).

*Venation pattern*.—Pinnate, veins barely visible. Midrib depressed on adaxial surface, raised 0.5 mm on abaxial surface.

*Vein color* (*midrib, both surfaces*).—150C.
*Foliar fragrance*.—None observed.

Spines:
*Shape*.—Terete.
*Dimensions*.—Up to 55 mm in length, 3 mm in diameter at base. Very sharp acute apex.
*Color*.—Ranges between 147B and 147A except 178D close to apex (5 mm from apex) and at apex.

Inflorescence, flowers:
*Inflorescence type*.—Solitary flowers, rotate, borne at branch terminals or at axil of spines.
*Inflorescence dimensions*.—4 cm to 7 cm in diameter across furthest petal apices.
*Flower quantity*.—Few, sparse. Plants may bear only one flower, or be devoid of flowers after latest summer flowering.
*Blooming season*.—Mid-April to late June.
*Flower shape*.—Rotate.
*Flower dimensions*.—4 cm to 7 cm in diameter, 6 cm in height including corolla tube.

Corolla:
*Shape*.—Narrowly cylindrical, formed of 4 fused lanceolate petals.
*Dimensions*.—5 mm in diameter at calyx, tapering to 2 mm to 3 mm in diameter at corolla tube mouth.
*Color* (*outer surfaces*).—N144D.
*Color* (*tube inner surface*).—1A.
*Surface*.—Outer surface, glabrous; inner surface lightly pubescent, hairs fine, white.

Petals:
*Quantity*.—4.
*Petal shape*.—Linear to very narrow lanceolate.
*Petal arrangement*.—Rotate, propeller-like.
*Petal color* (*adaxial and abaxial surfaces*).—Pure white, NN155D.
*Petal length*.—15 mm to 24 mm in length from mouth of corolla tube to apex.
*Petal width*.—3 mm to 4 mm.
*Petal apex*.—Acute.
*Petal base* (*at base of corolla tube petal*).—Obtuse.
*Petal margin*.—Entire.
*Petal surface* (*adaxial and abaxial surfaces*).—Glabrous.
*Peduncle length*.—Average is 4 mm.
*Peduncle diameter*.—0.5 mm.
*Peduncle color*.—138B.
*Peduncle shape*.—Cylindrical.
*Peduncle surface*.—Smooth.

Calyx:
*Shape*.—Funnelform.
*Calyx diameter* (*when flattened*).—7 mm.
*Calyx color*.—138B.

Sepals:
*Quantity*.—5.
*Shape*.—Ovate or lanceolate.
*Apex*.—Acuminate.
*Base*.—Truncate.
*Sepals fused or unfused*.—Unfused.
*Sepal dimensions*.—4 mm to 5 mm in length, 2.5 to 3.0 mm in width.
*Sepal margin*.—Entire.
*Sepal color* (*adaxial and abaxial surfaces*).—138B.
*Sepal apex*.—Acute.
*Sepal surface*.—Smooth.

Bud:
*Shape*.—Cylindrical, hemispherical apex.
*Dimensions*.—10 mm to 12 mm in length, 4 mm in diameter.
*Bud color*.—145C.
*Bud surface*.—Longitudinal parallel striations where petals are tightly fused.
*Flower fragrance*.—Sweet citrus fragrance, stronger in the evening.

Reproductive organs: Flowers are heteromorphic, in which the stamens and pistil vary in length from flower to flower. The single observed flower bore very short stamens and pistil.
*Stamens*.—6 in number, adnate to inside of corolla tube and not extending into corolla tube mouth.
*Filaments, anthers, pistil*.—Tiny and not closely observed, less than 1 mm in length and diameter.
*Pollen*.—None observed.
*Ovary shape*.—Not observed.

Fruit:
*Shape*.—Ovoid berry, apex acuminate, 4 mm in height, 3 mm in diameter when fully developed.
*Surface*.—Glossy.
*Color*.—64C.
*Seeds*.—Very few present and observed immature (soft) only.
*Shape*.—Ovoid up to 3 mm in length.
*Seed color*.—N144A.

COMPARISON WITH KNOWN VARIETY

'Lemon Twist' can be compared to the commercial variety 'Green Carpet' (not patented). Differences between the two varieties are described in Table 1:

TABLE 1

| 'Green Carpet' | 'Lemon Twist' |
|---|---|
| Green foliage | Variegate foliage. Green with cream edge. |
| Open habit. | Tighter habit. |

I claim:

1. A new and distinct cultivar of *Carissa* Plant Named 'Lemon Twist' as described and illustrated herein.

* * * * *